(12) United States Patent
Wei et al.

(10) Patent No.: US 6,319,900 B1
(45) Date of Patent: Nov. 20, 2001

(54) INHIBITION OF ABNORMAL CELL GROWTH WITH CORTICOTROPIN-RELEASING HORMONE ANALOGS

(75) Inventors: Edward T. Wei, Berkeley, CA (US); Andrzej T. Slominski, Glen Ellyn, IL (US)

(73) Assignees: The Regents of the University of California, Oakland, CA (US); Loyola University of Chicago, Maywood, IL (US)

( * ) Notice: Subject to any disclaimer, the term of this patent is extended or adjusted under 35 U.S.C. 154(b) by 0 days.

(21) Appl. No.: 09/400,716

(22) Filed: Sep. 21, 1999

(51) Int. Cl.$^7$ .................................................. C02K 14/00
(52) U.S. Cl. ............................ 514/12; 530/300; 530/306
(58) Field of Search .................................. 530/306, 300; 514/2, 12, 14

(56) References Cited

U.S. PATENT DOCUMENTS

| | | | |
|---|---|---|---|
| 5,480,869 | 1/1996 | Wei et al. | 514/12 |
| 5,777,073 | * 7/1998 | Rivier et al. | 530/306 |
| 5,844,074 | 12/1998 | Rivier | 530/306 |
| 5,869,450 | 2/1999 | Wei et al. | 514/12 |

OTHER PUBLICATIONS

Theoharides et al., "Corticotropin–releasing hormone induces skin mast cell degranulation and increased vascular permeability, a possible explanation for its proinflammatory effects", Endocrinology vol. 139 (1) pp. 403–413, 1998.*

Koerber et al., "Constrained Corticotropin–Releasing Factor (CRF) Agonists and Antagonists with i–(i+) Glu–Xaa–DX-bb–Lys Bridges," *J. Med. Chem., 41*, pp. 5002–5011, 1998.

Kornreich et al., "Alanine Series of Ovine Crticotropin Releasing Factor (oCRF): A Structure–Activity Relationship Study," *J. Med. Chem., 35*, pp. 1870–1876, 1992.

Tjuvajev et al., "Anti–Neoplastic Properties of Human Corticotropin Releasing Factor: Involvement of the Nitric Oxide Pathway," in vivo, 12, pp. 1–10, 1998.

Wei and Thomas, "Correlation of Neuroendocrine and Anti–Edema Activities of Alanine–Corticotropin–Releasing Factor Analogs," *European Journal of Pharmacology*, 263, pp. 319–321, 1994.

Wei et al., "D–Amino Acid–Substituted Analogs of Corticotropin–Releasing Hormone (CRH) and Urocortin with Selective Agonist Activity at $CRH_1$ and $CRH_{2\beta}$ Receptors," *Peptides*, 19:7, pp. 1183–1190, 1998.

* cited by examiner

*Primary Examiner*—Karen Cochrane Carlson
(74) *Attorney, Agent, or Firm*—Heller Ehrman White & McAuliffe LLP

(57) ABSTRACT

The glutamic acid residue of corticotropin-releasing hormone analogs have had the position 20 amino acid residue replaced with a D-amino acid moiety. The resulting CRH analogs do not significantly lower blood pressure but have anti-proliferative actions in cell culture and inhibit experimental cancer growth in animals (mice and rats). Novel applications of such analogs are described, such as to inhibit abnormal cell proliferation for conditions such as cancer, including melanoma, and for inflammatory dermatoses, such as psoriasis.

17 Claims, 2 Drawing Sheets

FIG._1

INHIBITION OF ABNORMAL CELL GROWTH WITH CORTICOTROPIN-RELEASING HORMONE ANALOGS

FIELD OF THE INVENTION

The invention generally relates to treatments for abnormal cell proliferation, particularly for treating epidermal disorders, and more particularly relates to a method of inhibiting abnormal cell growth with the use of certain corticotropin-releasing hormone ("CRH") analogs. Inhibition of abnormal cell growth has therapeutic utility in conditions such as cancer and psoriasis.

BACKGROUND OF THE INVENTION

Corticotropin-releasing hormone (CRH, also called CRF or corticoliberin) was first characterized as a 41-residue peptide isolated from ovine hypothalami by Vale et al. (1981). Subsequently, the sequence of human-CRH was deduced from cDNA studies and shown to be identical to rat-CRH, and then caprine, bovine, porcine, and white sucker fish CRH were characterized. The CRH of hoofed animals show considerable differences from man, but the pig and fish sequences differ from the human/rat sequence by only 2 out of 41 residues.

For some mysterious reason, peptides with homologous structures to mammalian CRH are found in cells of certain frog skins and in the urophysis of fish. In fact, the structure of sauvagine, the 40-amino acid peptide isolated from the skins of Phyllomedusa frogs, was reported several years before Vale's description of ovine-CRH. The structure of sucker fish urotensin I was reported just months after the description of ovine-CRH and resulted from an independent line of inquiry by Lederis's group in Canada. Although sauvagine and urotensin I release adrenocorticotropin (ACTH) from the pituitary, the functions of these peptides in the tree-frog (Phyllomedusa species that live in arid regions of South America) and in the sucker fish remain unknown.

In humans CRH regulates, via release of proopiomelanocortin, ACTH secretion from the anterior pituitary and has several direct actions on central and peripheral tissues. CRH has also been found to have direct anti-inflammatory properties. More recently, evidence has been provided that mammalian skin cells both produce CRH and express functional CRH receptors (Slominski et al., *FEBS Lett.*, 374, pp. 113–116, 1995; Slominski et al., *J. Clin. Endocrinol. Metab.*, 83, pp. 1020–1024, 1998; Slominski et al., *Hum. Pathol.*, 30, pp. 208–215, 1999), although it was not known whether locally produced CRH had an additional role in the physiology of the skin, other than as a vasodilator and inhibitor of thermal injury-induced edema.

Some therapeutic methods and uses for CRH are described by inventors Wei and co-workers in U.S. Pat. No. 4,801,612, issued Jan. 31, 1989, titled "Method of Inhibiting Inflammatory Response," and U.S. Pat. No. 5,137,871, issued Apr. 26, 1994, titled "Treatment to Reduce Edema for Brain and Musculature Injury." These patents describe the use of CRH to decrease the leakage of blood components into tissues produced by various adverse medical conditions, and thus to treat a patient for injury to or disease of the brain, central nervous system or musculature in which edema is a factor.

U.S. Pat. No. 5,869,450, issued Feb. 9, 1999, inventors Wei et al., describes CRH analogs in which the fifth amino acid from the N-terminus is D-Pro or in the case of urocortin or sauvagine where the fourth amino acid from the N-terminus is D-Pro or D-Ser. These analogs have an anti-inflammatory activity and a disassociated ACTH response.

Cyclic CRH agonists have recently been described by Rivier et al. (U.S. Pat. Nos. 5,844,074 and 5,824,771). These CRH analogs, modified by cyclization of residues 30–33 of CRH via a glutamic acid-lysine bridge, are more potent than native CRH in the release of ACTH and have lower molecular weight than native CRH. The elimination of residues 1–3 or 1–11 at the N-terminus of CRH has been shown to not alter biological activities or ACTH-release potency.

TABLE 1

Peptides of the Corticotropin-Releasing Hormone Superfamily

| SEQ. ID NO. | PEPTIDE | SPECIES | SEQUENCE[a,b] |
|---|---|---|---|
| 1 | CRH | Human/rat | SEEPPISLDL TFHLLREVLE MARAEQLAQQ AHSNRKLMEIJ |
| 2 | CRH | Pig | SEEPPISLDL TFHLLREVLE MARAEQLAQQ AHSNRKLMENF |
| 3 | CRH | Sucker fish | SEEPPISLDL TFHLLREVLE MARAEQLAQQ AHSNRKMMEIF |
| 4 | CRH | Sheep/goat | SQEPPISLDL TFHLLREVLE MTKADQLAQQ AHSNRKLLDIA |
| 5 | CRH | Cow | SQEPPJSLDL TFHLLREVLE MTKADQLAQQ AHNNRKLLDIA |
| 6 | Urotensin I | Sucker fish | NDDPPISIDL TFHLLRNMIE MARIENEREQ AGLNRKYLDEV |
| 7 | Urotensin I | Carp | NDDPPISIDL TFHLLRNMJE MARIENEREQ AGLNRKYLDEV |
| 8 | Urotensin I | Maggy sole | SEEPPMSJDL TFHMLRNMIH RAKMEGEREQ ALJNRNLLDEV |
| 9 | Urotensin I | European flounder | SEDPPMSIDL TFHMLRNMJH MAKMEGEREQ AQINRNLLDEV |
| 10 | Urocortin | Rat | DDPPLSIDL TFHLLRTLLE LARTQSQRER AEQNRJIFDSV |
| 11 | Urocortin | Human | DNPSLSIDL TFHLLRTLLE LARTQSQRER AEQNRIJFDSV |
| 12 | Sauvagine | Frog | >EGPPISJDL SLELLRKMIE IEKQEKEKQQ MNNRLLLDTI |

[a]The carboxyl termini of these peptides are amidated.
[b]Single letter abbreviations for amino acids: S, T, P, A, G; Ser, Thr, Pro; Ala, Gly; M, L, I, V; Met, Leu, Ile, Val; E, D, N, Q; Glu, Asp, Asn, Gln; R, K, H; Arg, Lys, His; F, Y, W, Phe, Tyr, Trp; >E; pyroglutamyl (Kornreich et al., *J. Med. Chem.*, 35, pp. 1870–1876, 1992; Koerber et al., *J. Med. Chem.*, 41(25), pp. 5002–5011, 1998.)

Recently, Tjuvajev et al. (Tjuvajev, J., Kolesnikov, Y., Joshi, R., Sherinski, J., Koutcher, L., Zhou, Y., Matei, C., Koutcher, J., Kreek, M. J., and Blasberg, R. Anti-neoplastic properties of human corticotropin releasing factor: involvement of the nitric oxide pathway. In Vivo., 12, pp.1–10, 1998. Department of Neurology, Memorial Sloan Kettering Cancer Center, New York, N.Y. 10021, USA) have introduced yet another novel mechanism for CRH in the form of anti-cancer action. Tjuvajev et al. (1998) reported a series of in vivo and in vitro studies that evaluated the anti-neoplastic potential of CRH in W256 rat mammary carcinoma. Using magnetic resonance imaging (MRI) and direct measurements of tumor and peritumoral brain water content they found that CRH treatment (100 micrograms/kg subcutaneously twice a day for 3 days) caused significant inhibition of growth of intracerebrally-injected W256 tumor cells. CRH also exhibited antiproliferative effects in in vitro cultures of W256 cells. The antiproliferative effects of CRH in W256 cells involve activation of nitric oxide synthase (NOS) and L-arginine-NO pathways. CRH activated the release of NO in W256 cells. The NO then became cytotoxic to the cancer cells.

Human trials of CRH for the treatment of peritumoral brain edema have been initiated and preliminary data indicated that CRH reduced brain edema associated with tumor metastases. However, the limiting factor on the use of CRH has been the known blood-pressure lowering property of CRH. CRH causes relaxation of smooth muscles surrounding blood vessels and causes vasodilation, resulting in a lowering of blood-pressure. The hypotension so produced is sufficiently dangerous to limit the dosages of CRH that can be administered to humans. If this dose-limiting toxicity is overcome by improved molecular design of CRH superfamily molecules, then it is conceivable that these analogs will have a higher therapeutic index and have utility via the anti-proliferative mechanism of action.

SUMMARY OF THE INVENTION

In one aspect of the present invention, a method of inhibiting abnormal cell proliferation in a patient diagnosed as being at risk of such condition is provided. In another aspect, practice of the invention provides a method of treating excessive epidermal proliferation. In yet another aspect of this invention, a kit is provided that is useful for treating a patient suffering from an abnormal cell proliferation conditions. The kit includes a pharmaceutically acceptable formulation of a corticotropin-releasing hormone ("CRH") analog where the analog has a D-configuration amino acid residue at a particular location of the sequence, and the kit further includes instructional materials for therapeutic use of the pharmaceutically formulated peptide.

These inventive aspects relate to our having found that replacement of the glutamic acid residue at position 20 of CRH to a D-amino acid moiety creates a molecule that has minimal activity to lower blood pressure, but the molecule retains anti-proliferative actions in cell culture and inhibits experimental cancer growth in animals (mice and rats).

Thus, novel applications of [D-Xaa$^{20}$]-substituted analogs of CRH, such as a preferred embodiment [D-Glu$^{20}$], are herein described in which the ability to inhibit abnormal cell proliferation with reduced hypotension is utilized. The peptide analogs, such as are exemplified by [D-Glu$^{20}$] CRH, have amino acid sequences of the CRH superfamily but wherein at least one amino acid residue at the 20 position has been replaced with a D-amino acid residue (however, peptides having 40 amino acid residues have the nineteenth such residue from the N-terminus modified by inclusion of a D-amino acid).

Among the novel uses of these peptide analogs are for the treatment of cancer and psoriasis, yet while avoiding the hypotensive properties of the normal CRH.

DETAILED DESCRIPTION OF THE PREFERRED EMBODIMENTS

Figure 1:
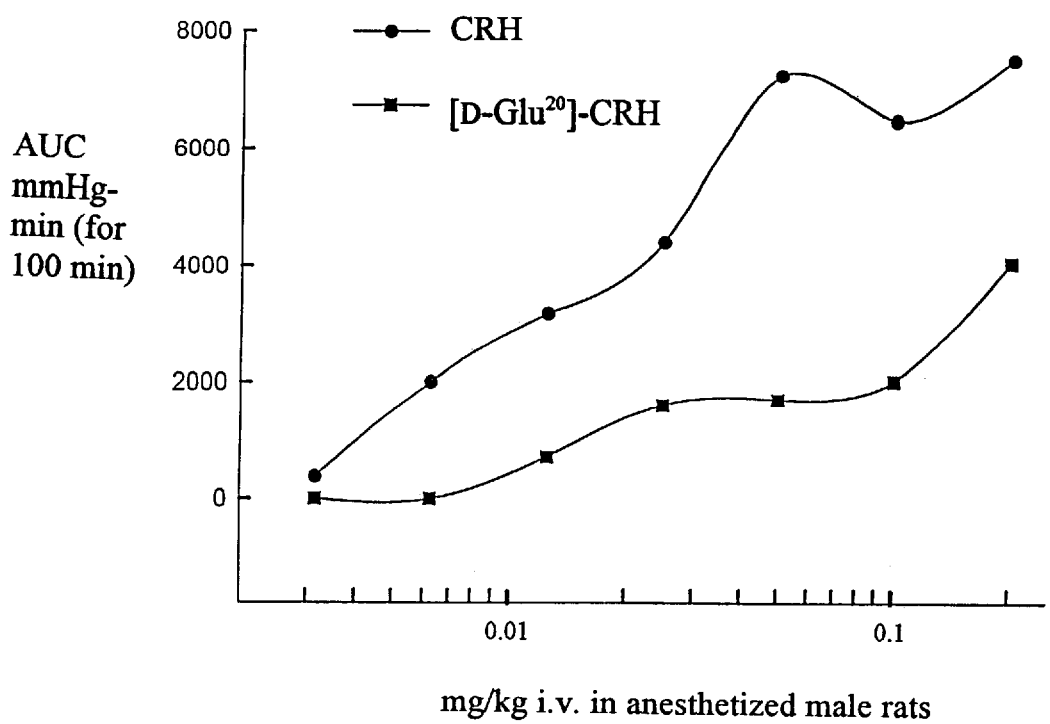
FIG. 1 graphically illustrates the hypotensive effects of unmodified CRH by contrast to the effect of [D-Glu$^{20}$]-CRH in anesthetized male rats.; and, FIG. 2 graphically illustrates inhibition of cell proliferation by administrations of a preferred embodiment in accordance with the invention.

The present invention describes novel actions of and applications for CRH compounds that are analogs of the CRH superfamily of peptides. By "CRH superfamily" is meant to include those peptides recognized by the art as belonging to the CRH family due to many sequence similarities and similar biological activities. These include the peptides illustrated by Table 1. Thus, the CRH superfamily includes the CRH peptides originating with or derived from a number of species, e.g., rat, human, pig, sheep, cow, and fish, and also includes sauvagine, urotensin I, and most recently urocortin. Urocortin is a mammalian neuropeptide described by Vaughan et al., *Nature*, 378, pp. 287–292 (1995).

The CRH peptides of this invention are based upon our discovery that replacing the twentieth amino acid (in the case of those 41 amino acid residue containing peptides of this family) with a D-amino acid reduces blood-pressure lowering yet while providing anti-neoplastic and anti-cell proliferative activities. Similarly, replacing the 19th residue of peptides having 40 amino acid residues with a D-amino acid residue also reduces blood pressure lowering yet provides anti-neoplastic and anti-cell proliferative activities.

We believe that the chirality of amino acid residue 20 is a more important determinant of activity (such as at the CRH$_2\beta$ receptor) than the acidic function (of the normal 20 position glutamic acid) or than the longer aliphatic side chain (or skeleton) of the glutamic acid residue. In other words, we believe that the 20$^{th}$ position is highly specific and that the recognition site does not particularly distinguish between amino acid residue structures, but instead primarily distinguishes between chiralities. Accordingly, we believe that substantially all peptides of this invention that have a D-orientation on the α-carbon of the amino acid residue at position 20 are suitable.

Also, among the CRH analogs described in the art are those including cyclic bonds, such as between the residues in the 30 and 33 position, which may be a disulfide linkage (between two Cys residues) but preferably where each is an amide-bond (i.e., a lactam bridge). Suitable such cyclic analogs of the CRH family of peptides are those described by U.S. Pat. No. 5,844,074, issued Dec. 1, 1998, inventor Rivier, which is incorporated herein by reference. Uses of such cyclic analogs are suitable in practicing the subject invention, if such cyclic analogs also have a D-amino acid substitution at the 20th amino acid (in the case of those 41 amino acid residue containing the peptides of the family).

Two examples of such suitable cyclic peptides are: Cyclo (30–33)-Acetyl-Pro$^4$, D-Phe$^{12}$, D-Glu$^{20}$, Nle$^{21,38}$, Glu$^{30}$, D-His$^{32}$, Lys$^{33}$-hCRH(4–41); and Cyclo(30–33)-Acetyl-Pro$^4$, D-Phe$^{12}$, D-Glu$^{20}$, Nle$^{18,21}$, Glu$^{30}$, D-Ala$^{32}$, Lys$^{33}$-carp urotensin (4–41).

The suitable neuropeptides should be administered under the guidance of a physician, and kits for practicing the invention are contemplated which include instructional materials. When treating disorders on the surface of the skin, the administration is preferably topical. Administration can be intermittent or continued after diagnosis of the premalignant, neoplastic or psoriatic condition, until there is alleviation of symptoms or signs of the diseases.

One aspect of the present invention is to provide a kit in which a pharmaceutically suitable formulation of the peptide (that is, the CRH analog) is one component of the kit while accompanying the peptide are instructional materials for therapeutic use of the so-formulated peptide. Instruction includes mode and manner of administration, dosages, frequency, contra Indications, and the like. For example, the instructional materials of such a kit instruct the patient in the appropriate dose and regime for administering the peptide. Therapeutically effective dosages are discussed hereinafter.

While the instructional materials typically comprise written or printed materials, they are not limited to such. Any medium capable of storing such instructions and communicating them to an end user is contemplated by this invention. Such media include, but are not limited to magnetic storage media (e.g., magnetic discs, tapes, cartridges, etc.) electronic storage media (e.g., memory chips, processing chips, etc.) optical media (e.g., holographic media, CD ROM, etc.), and the like. Such media may include addresses and/or hotlinks to global electronic access sites that provide such instructional materials.

Because peptides of this invention have the property of inhibiting abnormal cell proliferation, they are useful in a number of different therapeutic applications. Specific tissues for which clinical usage of these peptides may be applied include skin, as well as its adnexal structures such as hair follicle and sebaceous glands, and other epithelial tissues (eyelids, nasal membranes, oropharyngeal membranes, upper respiratory tract, esophagus, lower digestive tract), skeletal muscle, smooth muscle, cardiac muscle, blood vessels of the brain, and blood vessels of the lungs and kidneys. Where the tissues are not readily reached by topical administration (such as by creams and the like as further described hereinafter), then parenteral or systemic administration may be used.

For example, therapeutic uses of these peptides include administration to treat disseminated cancer, including melanoma, squamous cell carcinoma, breast cancer, premalignant lesions such as lentigo maligna, actinic keratosis, and, for non-cancerous conditions, such as psoriasis, eczema, alopecia areata, hypertrichosis or keloids. The keratinocytes are cells that line the base of the epidermis and form new cells which cover the surface of the body. These cells have a high metabolic activity and turnover; moreover, they participate in the inflammatory response, as they actively secrete cytokines and attract other inflammatory cells from the body (white blood cells). A disruption of keratinocyte activity is prominent in inflammatory dermatoses, of which psoriasis is a primary example. Other related conditions are eczema and various forms of dermatitis. Thus, an agent which inhibits keratinocyte proliferation is an useful agent for therapy of inflammatory dermatoses. For example, the basic lesion in psoriasis is hyperproliferation of keratinocytes in the epidermis. The turnover rate of these cells may be ten times more rapid than usual, and maturation of the cells is abnormal. (J. H. Stein, editor, *Internal Medicine*, chapter 216, "Psoriasis," pp. 1300–1302, 1998.)

The hair follicle—sebaceous gland unit of the skin, part of the "adnexa" or appendages of the skin is of pharmacological interest for these reasons:

(a) a large peptide such CRH, with a molecular weight of 4754 daltons, can get to targets because it can be formulated to sit on the skin and penetrate along the hair shaft to the base of the hair follicle and to the sebaceous gland;

(b) proliferation of hair follicle cells can result in hypertrichosis, so a peptide like CRH may have value as a means for stopping excessive hair growth;

(c) proliferation of lymphocytes at the base of the hair follicle, a condition called lymphocytosis, poses a much serious problem—a condition called alopecia areata—in which there is excessive hair loss. This frequently occurs in women under stress, and causes a strong emotional response, as the hair comes off in clumps and is cosmetically disfiguring. Current treatment is to use a steroid cream—but it is of limited effectiveness and not quick in onset;

(d) proliferation of the epithelial cells of the sebaceous gland during puberty and other conditions of excessive dihydrotestosterone production contributes to the condition known as acne.

Doses and Deliveries

Typically a therapeutically effective dosage is formulated to contain a concentration of at least about 0.1% w/w up to about 50% w/w or more, preferably more than 1% w/w of the active compound to the treated tissue. The active ingredient may be administered at once, or may be divided into a number of smaller doses to be administered at intervals of time or be administered as a sustained dose preparation. The term "sustained release formulation" is intended to encompass formulations that allow the continuous delivery of a CRH agonist to a subject over a period of time, preferably several days to weeks. Such formulations are typically administered subcutaneously or intramuscularly and allow for the continual steady release of a predetermined amount of drug in the subject over time. The sustained-release formulation of CRH agonist can be, for example, a formulation comprising a polymer selected from the group consisting of a poly-lactide polymer, a poly-glycolide polymer, and a poly-lactide/poly-glycolide copolymer (e.g., the drug is encapsulated within a microcapsule comprising the polymer or copolymer). Such sustained-release formulations, suitable for depot injection, are known in the art for administration of peptide agonists, such as leuprolide (e.g. U.S. Pat. Nos. 4,677,191 and 4,728,721). The sustained-release formulation can be formulated to allow for delivery of the drug over a predetermined time period. Alternatively, the sustained-release formulation of CRH agonist may comprise a formulaic in an osmotic pump (i.e., the CRH formulation is enclosed with the osmotic pump). Such osmotic pumps, which can be formulated to allow for release of a predetermined amount of drug over a predetermined time period, are known in the art (e.g. the Alzet pump, commercially available from Alza, Palo Alto, Calif.). The dosage of CRH agonist released by the sustained-release formulation is preferably about 5–300 microgram/kg/day, and more preferably 10–50 microgram/kg/day.

It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the proliferative condition and may be empirically determined.

Compounds are typically included at concentrations 0.001% w/w or greater than 1% w/w up to 50% w/w or higher. The concentration is generally greater than the concentration for systemic administration of the compound. Preferable concentrations are in the range of 0.01% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

Formulations

The suitable therapeutic formulations may be a solution, suspension, emulsion or the like, and may be formulated as creams, gels, ointments, emulsions, solutions, elixirs, lotions, suspensions, tinctures, pastes, foams, aerosols, irrigations, sprays, suppositories, bandages, or any other formulations suitable for topical, intravenous, intradermal, or subcutaneous injection administration.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an anti-proliferative effective amount of one or more of the compounds selected as described herein, in an effective concentration range (by weight), between about 0.1% and 80%, preferably 0.1 to 50%, more preferably greater than about 1% up to about 50% or more in a cream, ointment, lotion, gel, solution or solid base or vehicle known in the art to be nontoxic and dermatologically acceptable or suitable for application to the mucosa. Aqueous suspensions are preferably formulated at concentrations greater than about 1% w/w, more preferably 2% w/w.

To formulate a composition, the weight fraction of compound is dissolved, suspended, dispersed or otherwise mixed in a selected vehicle at an effective concentration such that the proliferative condition is relieved or ameliorated. Generally, emollient or lubricating vehicles that help hydrate the skin are more preferred than volatile vehicles, such as ethanol that dry the skin. Examples of suitable bases or vehicles for preparing compositions for use with human skin are petrolatum, petrolatum plus volatile silicones, lanolin, cold cream, and hydrophilic ointment.

The choice of an acceptable vehicle is largely determined by the mode of application and tissue to be treated. Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, skin penetration enhancers, coloring agents, fragrances, emulsifiers, thickening agents, and solvents.

Lotions

The lotions contain an effective concentration of one or more of the compounds. The effective concentration is preferably effective to deliver an anti-profliferative amount, typically at a concentration of between about 0.1–50% w/w or more of one or more of the compounds provided herein. The lotions also contain from 1% to 50% w/w, preferably from 3% to 15% w/w of an emollient and the balance water, a suitable buffer, a C.sub.2 or C.sub.3 alcohol, or a mixture of water of the buffer and the alcohol. Any emollients known to those of skill in the art as suitable for application to human skin may be used.

Creams

The creams are formulated to contain concentration effective to deliver an anti-proliferative effective amount of the compound to the treated tissue, typically at between about 0.1%, preferably at greater than 1% up to and greater than 50%, preferably between about 3% and 50%, more preferably between about 5% and 15% of one or more of the compounds provided herein. The creams also contain from 5% to 50%, preferably from 10% to 25%, of an emollient and the remainder is water or other suitable non-toxic carrier, such as an isotonic buffer. The cream may also contain a suitable emulsifier. The emulsifier is included in the composition at a level from 3% to 50%, preferably from 5% to 20%.

Solutions and suspensions for topical administration are formulated to contain an amount of one or more compounds effective to deliver an anti-proliferative amount, typically at a concentration of between about 0.1–50% w/w, preferably at least more than 1% w/w, more preferably more than 2% w/w of one or more of the compounds provided herein. The balance is water, a suitable organic solvent or other suitable solvent or buffer. Suitable organic materials useful as the solvent or a part of a solvent system are as follows: propylene glycol polyethylene glycol (M.W. 200–600), polypropylene glycol (M.W. 425–2025), glycerine, sorbitol esters, 1,2,6 -hexanetriol ethanol, isopropanol, diethyl tartrate, butanediol and mixtures thereof Such solvent systems can also contain water.

Solutions or suspensions used for local application can include any of the following components: a sterile diluent, such as water for injection, saline solution, fixed oil, polyethylene glycol glycerine, propylene glycol or other synthetic solvent; antimicrobial agents, such as benzyl alcohol and Methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Liquid preparations can be enclosed in ampoules, disposable syringes or multiple dose vials made of glass, plastic or other suitable material Suitable carriers may include physiological saline or phosphate buffered saline (PBS), and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

Suitably prepared solutions and suspension may also be topically applied to the eyes and mucosa. Solutions, particularly those intended for ophthalmicuse, maybe formulated as 0.01%–10% w/w isotonic solutions, pH about 5–7, with appropriate salts, and preferably containing one or more ofthe compounds herein at a concentration of about 0.1% w/w preferably greater than 1% w/w, up to 50% w/w or more. Suitable ophthalmic solutions are known (see, e.g. U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 AM dibasic sodium phosphate, 8–12 mM sodium citrate, 0.5–1.5 mM magnesium chloride, 1.5–2.5 mM calcium chloride, 15–25 MM sodium acetate, 10–20 mM D.L.-sodium .beta.-hydroxy butyrate and 5–5.5 mM glucose.

Gels

Gel compositions can be formulated by simply admixing a suitable thickening agent to the previously described solution or suspension composition. Examples of suitable thickening agents have been previously described with respect to the lotions.

The gelled compositions contain an effective amount of one or more of an anti-proliferative amount, typically at a concentration of between about 0.1– 50% w/w or more of one or more of the compounds provided therein; from 5% to 75% w/w, preferably from 10% to 50% w/w, of an organic solvent as previously described; from 0.5% to 20% w/w, preferably from 1% to 10% w/w of the thickening agent; the balance being water or other aqueous carrier.

Aspects of the invention will now be illustrated by the following examples, which are intended to illustrate but not to limit the invention.

EXAMPLE 1

This example illustrates the anti-cancer property of an inventive peptide with a D-amino acid as residue 20. Various tumor cells were transplanted into mice or rats and the tumor volume was measured using a caliper-ruler. The volume of the tumor, in cubic mm, was estimated as the long axis x the square of the short axis divided by 2.

In the experiment of Table 2, female mice, weighing 20–25 g, of a C57B1 line, were transplanted under the skin with B16 melanoma cells. After transplantation of tumors mice were mixed and divided into groups of controls, CRH-treated and [D-Glu$^{20}$] CRH-treated. The test substances at a dose of 0.1 mg/kg subcutaneously or the vehicle control (saline) was injected on days 3 to 7 after tumor transplantation, and the volume of tumors were measured at various days afterwards.

TABLE 2

Influence of CRH and [D-Glu$^{20}$] CRH on Growth of B16 Melanoma in Mice

| GROUPS | DOSE (mg/kg) | Volume of Tumors in mm$^3$ Days after transplantation of tumors | | | |
|---|---|---|---|---|---|
| | | 10 | 12 | 14 | 17 |
| Controls | — | 59 + 9 | 221 + 38 | 296 + 62 | 382 + 118 |
| hCRH | 0.1 | 29 + 7* | 157 + 23* | 133 + 15* | 238 + 41 |
| [D-Glu$^{20}$] CRH | 0.1 | 37 + 7* | 86 + 15* | 138 + 16* | 252 + 54 |

*significant reduction of tumor volume, P < 0.05

The second experiment and third experiment (data shown in Tables 3 and 4) were conducted on white non-inbred male rats with a subcutaneous transplant of Walker carcinosarcoma or Ehrlich solid carcinoma. Animals after transplantation of tumors were mixed and were divided into groups of controls, CRH-treated and [D-Glu$^{20}$] CRH-treated.

TABLE 3

Influence of CRH and [D-Glu$^{20}$] CRH on Growth of Walker Carcinosarcoma in Rats

| GROUPS | DOSE (mg/kg), N = no. of rats | Volume of Tumors in mm$^3$ Days after transplantation of tumors | | | |
|---|---|---|---|---|---|
| | | 7 | 10 | 12 | 14 |
| Controls | —, 8 | 345 ± 41 | 4288 ± 613 | 13193 ± 2361 | 14096 ± 1971 |
| hCRH | 0.1, 16 | 196 ± 35* | 3600 ± 413 | 6942 ± 905* | 10832 ± 1146 |
| [D-Glu$^{20}$] CRH | 0.1, 16 | 127 ± 22* | 3926 ± 633 | 6554 ± 1041* | 10191 ± 1260 |

*significant reduction of tumor volume, P < 0.05

TABLE 4

Influence of CRH and [D-Glu$^{20}$] CRH on Growth of Ehrlich Solid Carcinoma in Rats

| GROUPS | DOSE (mg/kg), N = no. of rats | Volume of Tumors in mm$^3$ Days after transplantation of tumors | | |
|---|---|---|---|---|
| | | 9 | 11 | 14 |
| Controls | —, 8 | 350 ± 13 | 776 ± 154 | 1265 ± 272 |
| hCRH | 0.1, 16 | 226 ± 14* | 384 ± 61* | 763 ± 114* |
| [D-Glu$^{20}$] CRH | 0.1, 16 | 283 ± 33* | 470 ± 80* | 571 ± 199* |

*significant reduction of tumor volume, P < 0.05

EXAMPLE 2

The peptide embodiment of the invention, [D-Glu$^{20}$] CRH, was prepared where the normal 20 position glutamic acid of CRH had been substituted with D-glutamic acid. FIG. 1 graphically illustrates the hypotensive effects of unmodified CRH by contrast to the effect of [D-Glu$^{20}$]-CRH in anesthetized male rats. On the ordinate, the response is given in units of integrated blood pressure observed over a 100 minute period after the intravenous injection of the test substance is pentobarbital-anesthetized rats (no. of animals=8 per group per dose). The area-under-curve, is given in units of mm Hg per minute. For example, at a dose of 0.05 mg/kg peptide i.v., the response is approximately 7200 mm Hg-min versus 1700 mm Hg-min for the D-amino acid substituted analog. That is, over a 100 minute period, the average fall in mean blood pressure is 72 mm Hg for CRH, but only 17 mm Hg for the D-amino acid substituted analog. This [D-Glu$^{20}$]-CRH analog embodiment of the invention provided much less hypotensive activity than that of the unmodified CRH (human/rat) control.

EXAMPLE 3

Example 3 illustrates an assay for the anti-proliferative property of the D-amino acid residue 20 substituted peptide for this invention. We have further tested embodiments for these anti-proliferative actions on human keratinocytes.

Methods and Materials

Human melanoma cells were maintained as monolayers in T25 culture flasks (Corning) in Ham's F-10 media with 10% fetal bovine serum, 10 μg/ml insulin, 250 U/ml penicillin G (Sigma), 50 U/ml polymyxin B sulfate (Sigma), 100 μg/ml streptomycin sulfate (Pfizer), 2.5 μg/ml amphotericin B, and 10 μg/ml gentamicin solution. Cloudman S91 melanoma cells had an additional 7% fetal horse serum added to the above formulation for optimal growth. Cells were incubated at 37° C. in a humid atmosphere of 5% $CO_2$ and 95% air.

For generation of growth curves, cells were seeded in 96-well tissue culture plates (Dynatech) at 2000 cells/well with the above media, except that 5% fetal bovine serum was used instead of 10%. Cells were allowed to attach overnight and 24 hours after seeding, a baseline reading of cells were taken using the Aqueous Cell Proliferation Assay Kit (Promega) based on the colorimetric assay method by Mosmann (Mosmann T: Rapid calorimetric assay for cellular growth and survival: application to proliferation and cytotoxicity assay. *J. Immunological Methods*, 65, pp. 55–66, 1983.). Ham's F-10 media with the above supplements with or without the [D-Glu$^{20}$] corticotropin releasing hormone (CRH) at the following concentrations: $10^{-6}$, $10^{-8}$ and $10^{-10}$ M for the duration of cell growth measurement. Cell growth was measured every 3–4 days using the Promega kit, absorbance measured at 492 nm on a Titertek Multiscan spectrophotometer, until cell death or maximum growth had been achieved. Plates were maintained in a 37° C. incubator also in a humid atmosphere of 5% $CO_2$ and 95% air. [D-Glu$^{20}$], CRH, at low concentrations was able to inhibit melanoma cell growth in vitro.

Keratinocytes Proliferation

Two protocols were applied. The cells were seeded into 24 well plates at the concentration of 50,000 cells/well in 0.5 ml of DMEM plus 5% FBS. Next day the media were changed to DMEM containing 5% fetal bovine serum (final volume of 200 μl) supplemented with $^3$H [methyl-$^3$H] thymidine (1 μCi/ml) and different concentrations of the [D-Glu$^{20}$] CRH. The cells were incubated for 6 hours, then the media were discarded, the wells washed twice with DMEM (1 ml), and the cells dissolved in 300 μl of 1 N NaOH. The resulting solution was mixed with liquid scintillation fluid and the radioactivity counted in the Beckman liquid scintillation spectrometer. Significant inhibition of DNA synthesis was noted at the concentration 1 nM of [D-Glu$^{20}$] CRH. The data is illustrated by FIG. 2.

The cells were seeded into 24 well plates at the concentration of 20,000 cells/well in 0.5 ml of DMEM plus 5% FBS. After 8 hours the media were changed and different concentrations of [D-Glu$^{20}$] CRH were added. After 24 hours the media were changed again and supplemented with different concentrations of [D-Glu$^{20}$] CRH as well as with $^3$H [methyl-$^3$H] thymidine (1 μCi/ml). The cells were incubated overnight, then the media were discarded, the wells washed twice with DMEM (1 ml), and the cells dissolved in 300 μl of 1 N NaOH. The resulting solution was mixed with liquid scintillation fluid and the radioactivity counted in the Beckman liquid scintillation spectrometer.

Figure 2:
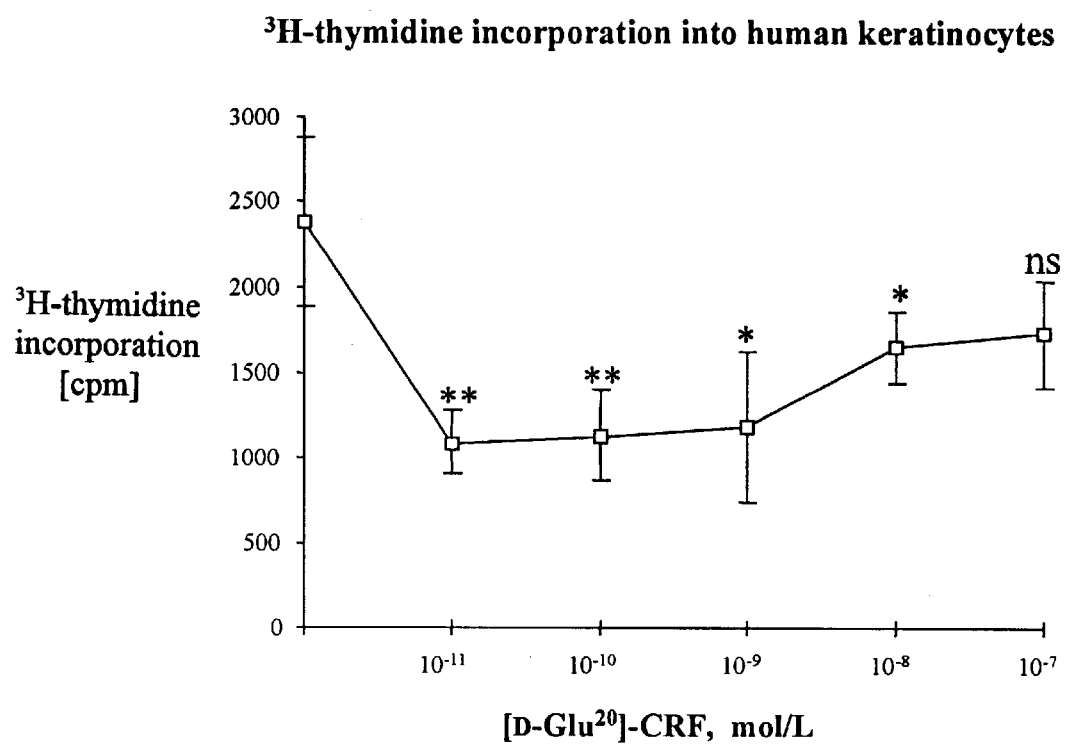

As shown by FIG. 2, significant and dose-dependent inhibition of cell proliferation as measured by DNA synthesis, was noted at the concentration as low as 10 pM of the ligand. The experiment was repeated with similar results.

It is to be understood that while the invention has been described above in conjunction with preferred specific embodiments, the description and examples are intended to illustrate and not limit the scope of the invention, which is defined by the scope of the appended claims.

---

It is claimed:

1. A method of treating a patient suffering from an inflammatory dermatoses psoriatic condition, comprising:
    administering to the patient a peptide analog of a Corticotropin-Releasing Hormone (CRH) having the amino acid sequence of human CRH (SEQ ID NO:1), but wherein the 20th amino acid from the N-terminus is a D-amino acid and wherein the analog provides an anti-proliferative activity for keratinocytes in vivo that is substantially free of hypotension.

2. The method as in claim 1, wherein the condition is cancerous.

3. The method as in claim 1, wherein the administering is by topical, intravenous, intradermal, or subcutaneous injection.

4. The method of claim of 3 wherein the analog administered is human/rat [D-Glu$^{20}$] CRH.

5. A method of inhibiting abnormal epidermal cell proliferation in a patient diagnosed at risk of same, comprising:
    administering an analog of corticotropin-releasing hormone (CRH), said analog having the 20$^{th}$ amino acid from the N-terminus of a 41 amino acid peptide of the corticotropin-releasing hormone superfamily or the 19$^{th}$ amino acid from the N-terminal of a 40 amino acid peptide of the corticotropin-releasing hormone superfamily is a D-configuration amino acid residue, wherein said analog inhibits abnormal epidermal cell proliferation.

6. The method as in claim 5, wherein the administering is to the skin or mucous membrane of the patient and the patient is diagnosed as being at risk of a melanoma.

7. The method as in claim 5 wherein the analog administered is in an amount of from about 0.001 mg to about 1.0 mg/kg/day of patient body weight.

8. The method as in claim 5 wherein the analog administered is Cyclo(30–33)-Acetyl-Pro$^4$, D-Phe$^{12}$, D-Glu$^{20}$, Nle$^{21,38}$, Glu$^{30}$, D-His$^{32}$, Lys$^{33}$-hCRH(4–41), or Cyclo(30–33)-Acetyl-Pro$^4$, D-Phe$^{12}$, D-Glu$^{20}$, Nle$^{18,21}$, Glu$^{30}$, D-Ala$^{32}$, Lys$^{33}$-carp urotensin (4–41).

9. The method as in claim 5 wherein the administering is topical, systemic or parenteral.

10. The method as in claim 5 wherein the analog administered is formulated for sustained-release.

11. The method as in claim 5 wherein the analog administered includes cyclic bonds.

12. The method as in claim 5 wherein the administering is intranasal.

13. The method as in claim 5 wherein the administering is intrabuccal.

14. A kit useful for treating a patient suffering from an excessive epidermal cell proliferation comprising:
    a pharmaceutically acceptable formulation containing a concentration of at least about 0.1% w/w of a CRH analog in which the 20$^{th}$ amino acid from the N-terminal is a D-configuration amino acid residue, the CRH analog providing an anti-proliferative activity for keratinocytes when appropriately administered; and
    instructional materials for appropriate administration in the therapeutic use of the pharmaceutically suitable formulation.

15. The kit as in claim 14 wherein the CRH analog is Cyclo(30–33)-Acetyl-Pro$^4$, D-Phe$^{12}$, D-Glu$^{20}$, Nle$^{21,38}$, Glu$^{30}$, D-His$^{32}$, Lys$^{33}$-hCRH(4–41), or Cyclo(30–33)-Acetyl-Pro$^4$, D-Phe$^{12}$, D-Glu$^{20}$, Nle$^{18,21}$, Glu$^{30}$, D-Ala$^{32}$, Lys$^{33}$-carp urotensin (4–41).

16. The kit as in claim 14 wherein the analog includes cyclic bonds.

17. The kit as in claim 14 wherein the formulation is adapted to topical administration and the instructional materials include instructions for topical administration.

\* \* \* \* \*

SEQUENCE LISTING

<160> NUMBER OF SEQ ID NOS: 12

<210> SEQ ID NO 1
<211> LENGTH: 41
<212> TYPE: PRT
<213> ORGANISM: Human/rat

<400> SEQUENCE: 1

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
             20                  25                  30

Ser Asn Arg Lys Leu Met Glu Ile Ile
         35                  40

<210> SEQ ID NO 2
<211> LENGTH: 41
<212> TYPE: PRT
<213> ORGANISM: Pig

<400> SEQUENCE: 2

-continued

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
             20                  25                  30

Ser Asn Arg Lys Leu Met Glu Asn Phe
         35                  40

<210> SEQ ID NO 3
<211> LENGTH: 41
<212> TYPE: PRT
<213> ORGANISM: Sucker fish

<400> SEQUENCE: 3

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
             20                  25                  30

Ser Asn Arg Lys Met Met Glu Ile Phe
         35                  40

<210> SEQ ID NO 4
<211> LENGTH: 41
<212> TYPE: PRT
<213> ORGANISM: Sheep/goat

<400> SEQUENCE: 4

Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
             20                  25                  30

Ser Asn Arg Lys Leu Leu Asp Ile Ala
         35                  40

<210> SEQ ID NO 5
<211> LENGTH: 41
<212> TYPE: PRT
<213> ORGANISM: Cow

<400> SEQUENCE: 5

Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
             20                  25                  30

Asn Asn Arg Lys Leu Leu Asp Ile Ala
         35                  40

<210> SEQ ID NO 6
<211> LENGTH: 41
<212> TYPE: PRT
<213> ORGANISM: Sucker fish

<400> SEQUENCE: 6

Asn Asp Asp Pro Pro Ile Ser Ile Asp Leu Thr Phe His Leu Leu Arg
 1               5                  10                  15

Asn Met Ile Glu Met Ala Arg Ile Glu Asn Glu Arg Glu Gln Ala Gly
             20                  25                  30

Leu Asn Arg Lys Tyr Leu Asp Glu Val
         35                  40

<210> SEQ ID NO 7

```
<211> LENGTH: 41
<212> TYPE: PRT
<213> ORGANISM: Carp

<400> SEQUENCE: 7

Asn Asp Asp Pro Pro Ile Ser Ile Asp Leu Thr Phe His Leu Leu Arg
 1               5                  10                  15

Asn Met Ile Glu Met Ala Arg Ile Glu Asn Glu Arg Glu Gln Ala Gly
            20                  25                  30

Leu Asn Arg Lys Tyr Leu Asp Glu Val
        35                  40

<210> SEQ ID NO 8
<211> LENGTH: 41
<212> TYPE: PRT
<213> ORGANISM: Maggy sole

<400> SEQUENCE: 8

Ser Glu Glu Pro Pro Met Ser Ile Asp Leu Thr Phe His Met Leu Arg
 1               5                  10                  15

Asn Met Ile His Arg Ala Lys Met Glu Gly Glu Arg Glu Gln Ala Leu
            20                  25                  30

Ile Asn Arg Asn Leu Leu Asp Glu Val
        35                  40

<210> SEQ ID NO 9
<211> LENGTH: 41
<212> TYPE: PRT
<213> ORGANISM: European flounder

<400> SEQUENCE: 9

Ser Glu Asp Pro Pro Met Ser Ile Asp Leu Thr Phe His Met Leu Arg
 1               5                  10                  15

Asn Met Ile His Met Ala Lys Met Glu Gly Glu Arg Glu Gln Ala Gln
            20                  25                  30

Ile Asn Arg Asn Leu Leu Asp Glu Val
        35                  40

<210> SEQ ID NO 10
<211> LENGTH: 40
<212> TYPE: PRT
<213> ORGANISM: Rat

<400> SEQUENCE: 10

Asp Asp Pro Pro Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 11
<211> LENGTH: 40
<212> TYPE: PRT
<213> ORGANISM: Human

<400> SEQUENCE: 11

Asp Asn Pro Ser Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
            20                  25                  30
```

-continued

```
Asn Arg Ile Ile Phe Asp Ser Val
            35                  40

<210> SEQ ID NO 12
<211> LENGTH: 40
<212> TYPE: PRT
<213> ORGANISM: Frog
<220> FEATURE:
<221> NAME/KEY: SITE
<222> LOCATION: (1)
<223> OTHER INFORMATION: Xaa in position 1 is pyroglutamyl

<400> SEQUENCE: 12

Xaa Gly Pro Pro Ile Ser Ile Asp Leu Ser Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40
```